(12) United States Patent
Alexander

(10) Patent No.: US 8,189,190 B2
(45) Date of Patent: May 29, 2012

(54) REMOTE CHEMICAL AND ELEMENTAL ANALYSIS BY ULTRA FAST SPECTROSCOPY

(75) Inventor: Dennis R. Alexander, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 987 days.

(21) Appl. No.: 11/848,886

(22) Filed: Nov. 2, 2007

(65) Prior Publication Data

US 2011/0001966 A1 Jan. 6, 2011

Related U.S. Application Data

(60) Provisional application No. 60/813,608, filed on Aug. 31, 2006.

(51) Int. Cl.
*G01J 3/18* (2006.01)

(52) U.S. Cl. ........................................................ 356/318

(58) Field of Classification Search .................. 356/318; 250/216

See application file for complete search history.

(56) References Cited

U.S. PATENT DOCUMENTS

| | | | | |
|---|---|---|---|---|
| 7,039,161 | B2 * | 5/2006 | Ito et al. ........................... | 378/86 |
| 7,336,988 | B2 * | 2/2008 | Schnitzer ....................... | 600/476 |
| 2002/0093632 | A1 * | 7/2002 | Teich et al. ..................... | 355/18 |
| 2003/0025911 | A1 * | 2/2003 | Walmsley et al. ............. | 356/450 |
| 2004/0207850 | A1 * | 10/2004 | Kwak et al. .................... | 356/432 |

* cited by examiner

*Primary Examiner* — Tarifur Chowdhury
*Assistant Examiner* — Abdullahi Nur
(74) *Attorney, Agent, or Firm* — Fish & Richardson P.C.

(57) ABSTRACT

Systems and methods are provided for monitoring materials using ultra fast laser pulses. Ultra fast laser pulses, such as femtosecond or attosecond laser pulses, are applied to the materials and laser pulses that result from interactions between the ultra fast laser pulses and the materials are collected. Spectral content of the resulting pulses is generated and presented. The elemental composition of the materials is determined using the spectral content.

27 Claims, 4 Drawing Sheets

US 8,189,190 B2

REMOTE CHEMICAL AND ELEMENTAL ANALYSIS BY ULTRA FAST SPECTROSCOPY

CROSS-REFERENCE TO RELATED APPLICATIONS

This application claims priority under 35 U.S.C. §119(e) from Provisional U.S. Application No. 60/813,608 filed on Aug. 31, 2006.

STATEMENT REGARDING FEDERALLY SPONSORED RESEARCH OR DEVELOPMENT

Not applicable.

BACKGROUND

There is a growing need to perform non-contact metrology in processing silicon carbide (SiC) power metal-oxide semiconductor field effect transistors (MOSFETs). For example, the department of defense is currently moving towards platforms and weapons systems that explore electrical powers in innovative ways. To reach the envisioned capabilities in electric propulsion and weapons in a tactical configuration, advances are necessary in the solid state power electronics used to distribute, condition, and regulate the electrical powers.

For instance, the concept of electric warships depends on the ability to rapidly switch power to major loads to meet tactical needs. Current approaches for power distribution being considered for the next generation of carriers and destroyers employ 13.8 kV AC power that is stepped down to 450 V AC by using large (6 ton and 10 m$^3$) 2.7 MVA transformers. The advanced power electronic components of interest under this effort should enable the realization of a solid state power substation (SSPS) that converts the distributed 13.8 kV AC power down to 450 V AC at the same total power level (2.7 MVA) as the current system with a reduction in size of 60% and reduction in weight of approximately 2.6 tons for a single 2.7 MVA transformer. To meet corresponding performance requirements, new wide band-gap semiconductor materials and devices, such as those based on SiC, are required.

Power switching devices and components fabricated from SiC offer a reduction in on-state resistance for high voltage components compared to silicon components. Furthermore, the SiC devices and components offer dramatically lower switching losses, allowing the use of higher frequency AC power; thereby enabling a reduction in the size and weight of passive components in a power conversion circuit. Finally, elevated junction temperature operating capacity up to at least 200 degree centigrade for SiC devices and components allows further reduction of the size of the cooling sub-system.

Under previously funded Department of Defense programs, critical SiC material metrics were demonstrated that have been deemed necessary to enable large area (i.e., 1 cm$^2$), high total power device. In these efforts, small-area devices consistent with the goals of high-voltage switching have been demonstrated in limited quantity. However, these demonstrations have not been consistent with a robust device process and high total power handling capability. Silicon carbide (SiC) MOSFETs, for example, have been demonstrated to exhibit breakdown voltage in excess of 10 kV and specific on-resistance less than 0.15 ohm-cm$^2$. However, issues of achieving high operating currents, stable threshold-voltages and proven reliability of MOS structures remain. Therefore, effort is needed to move beyond single device demonstrations and address manufacturing issues associated with improving the yield, performance, reliability, and cost of future high-power SiC based components. The traditional method used to monitor the quality of a metal-oxide semiconductor (MOS) stack involves at least three mask levels and several days of processing before providing the necessary feedback on the quality and functionality of the device being fabricated. Femtosecond laser induced breakdown spectroscopy (FLIBS) can be used to determine the elemental compositions of a MOSFET surface being fabricated, thereby monitoring the quality of the MOSFET surface. However, FLIBS analysis involves destroying a selected sample surface, such as MOSFET wafer. Capabilities of monitoring interfacial defects without damaging a surface involved, therefore, would advance the current state of the art.

SUMMARY

The present invention uses the wavelength spectrum in a femtosecond or attosecond laser pulse to perform remote non invasive analysis of surfaces, interfaces, clouds, chemical or biological warfare agents. The material to be analyzed is illuminated with the femtosecond attosecond laser pulses. The electromagnetic radiation transmitted, scattered, and/or reflected by the materials is analyzed for the spectral content after the interaction. The material property can be revealed by the spectral content after the illumination process. This will generally show up as a change in the amount of each spectral line that was contained in the pulse. The scattered and/or transmitted pulses are analyzed with a spectrum analyzer and an autocorrelator. The phase can also be used in an equivalent manner to reveal such things as chemical or elemental content.

In one aspect, an embodiment of the present invention relates to a method for monitoring a surface using ultra fast laser pulses. Ultra fast laser pulses are applied on at least a portion of a surface. Laser pulses that are reflected from the surface are collected. Spectral content of the reflected laser pulses are then presented.

In another aspect, an exemplary embodiment of the invention takes the form of a system for monitoring a surface using ultra fast laser pulses. The system includes a pulse generator and a pulse detector. The pulse generator is configured to generate ultra fast laser pulses and apply the ultra fast laser pulses on a surface. The pulse detector is configured to collect laser pulses that are reflected from the surface.

In yet another aspect, an exemplary embodiment of the invention takes the form of a method for monitoring a surface using ultra fast laser pulses. Pump-probing technique is performed on a surface by varying the time delay between a pump beam and a probe beam, wherein the pump beam and the probe beam comprise one or more of a sample of femtosecond laser pulses and a sample of attosecond laser pulses.

BRIEF DESCRIPTION OF THE SEVERAL VIEWS OF THE DRAWINGS

The present invention is described in detail below with reference to the attached drawing figures, which are incorporated by reference herein and wherein.

DETAILED DESCRIPTION

The present invention permits monitoring a surface using ultra fast laser pulses. As a result, among other things, the current invention provides non-contact metrology and non-contact pump-probing techniques using ultra fast laser pulses such as femtosecond laser pulses and attosecond laser pulses.

The subject matter of the present invention is described with specificity herein to meet statutory requirements. However, the description itself is not intended to limit the scope of this patent. Rather, the inventor has contemplated that the claimed subject matter might also be embodied in other ways, to include steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed.

Figure 1:
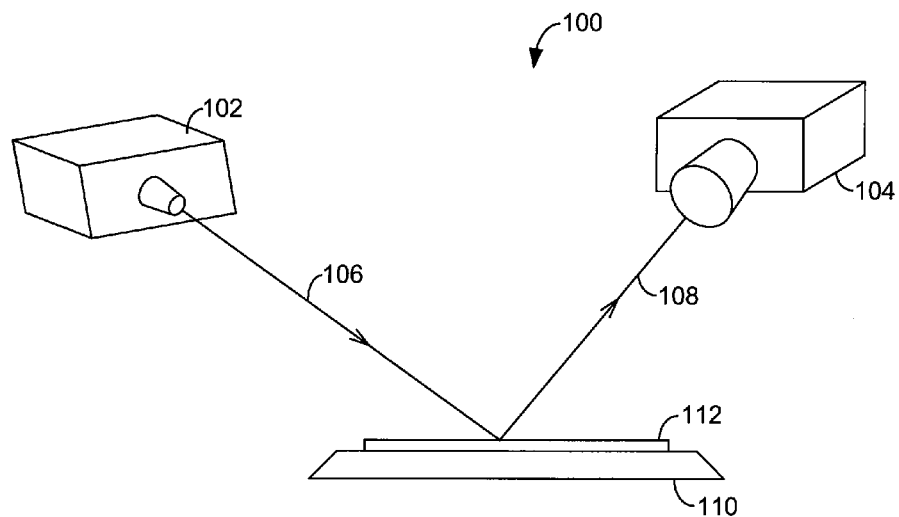
FIG. 1 is a block diagram of an exemplary system environment suitable for use in implementing the present invention.

Referring to FIG. 1, a block diagram is shown of an exemplary system environment 100 in which exemplary embodiments of the present invention may be employed. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components and in any suitable combination and location. Various functions described herein as being performed by one or more entities may be carried out by hardware, firmware, and/or software. For instance, various functions may be carried out by a processor executing instructions stored in memory.

As shown in FIG. 1, system environment 100 may include, among other components, an ultra fast pulse generator 102, a pulse detector 104, and a surface 110 to be analyzed. In some embodiments, the surface 110 is coated or covered with contaminants 112. Pulse generator 102 may apply a pulse 106 to surface 110 and potentially contaminants 112. After the photons interact with surface 110 and/or contaminants 112, the resulting pulse 108 may be collected by pulse detector 104 for analysis.

Figure 2:
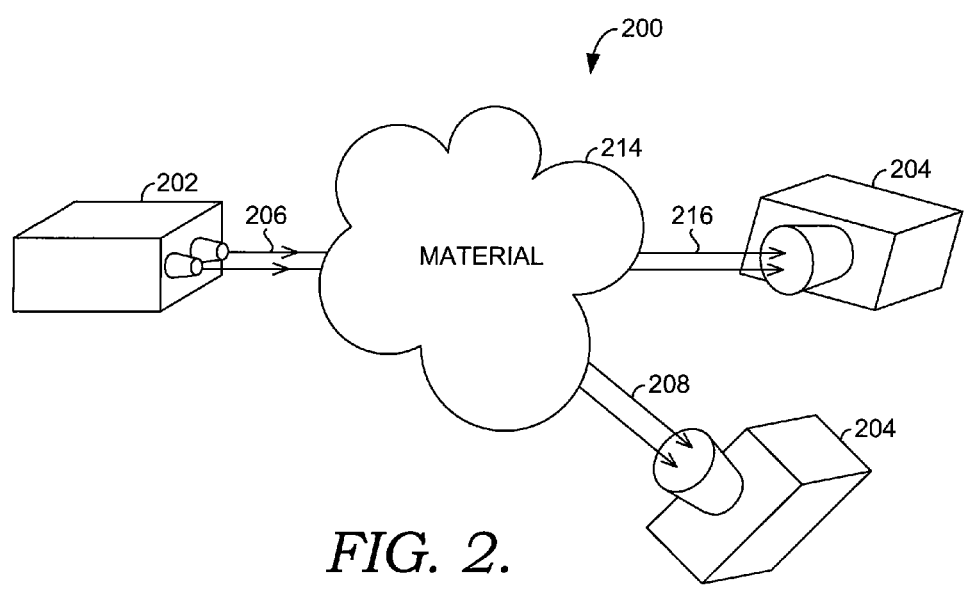
FIG. 2 is a block diagram of an exemplary system environment suitable for use in implementing the present invention.

As shown in FIG. 2, a further system environment 200 may include an ultra fast pulse generator 202, one or more pulse detectors 204, and materials 214 to be analyzed. Materials 214 may comprise clouds of chemical and/or biological compounds/agents. Pulse generator 202 may apply a pulse 206 to material 214. After the photons interact with materials 214, the resulting pulse 216 and/or scattered pulse 208 may be collected by one or more pulsed detector 204 for analysis.

Figure 3:
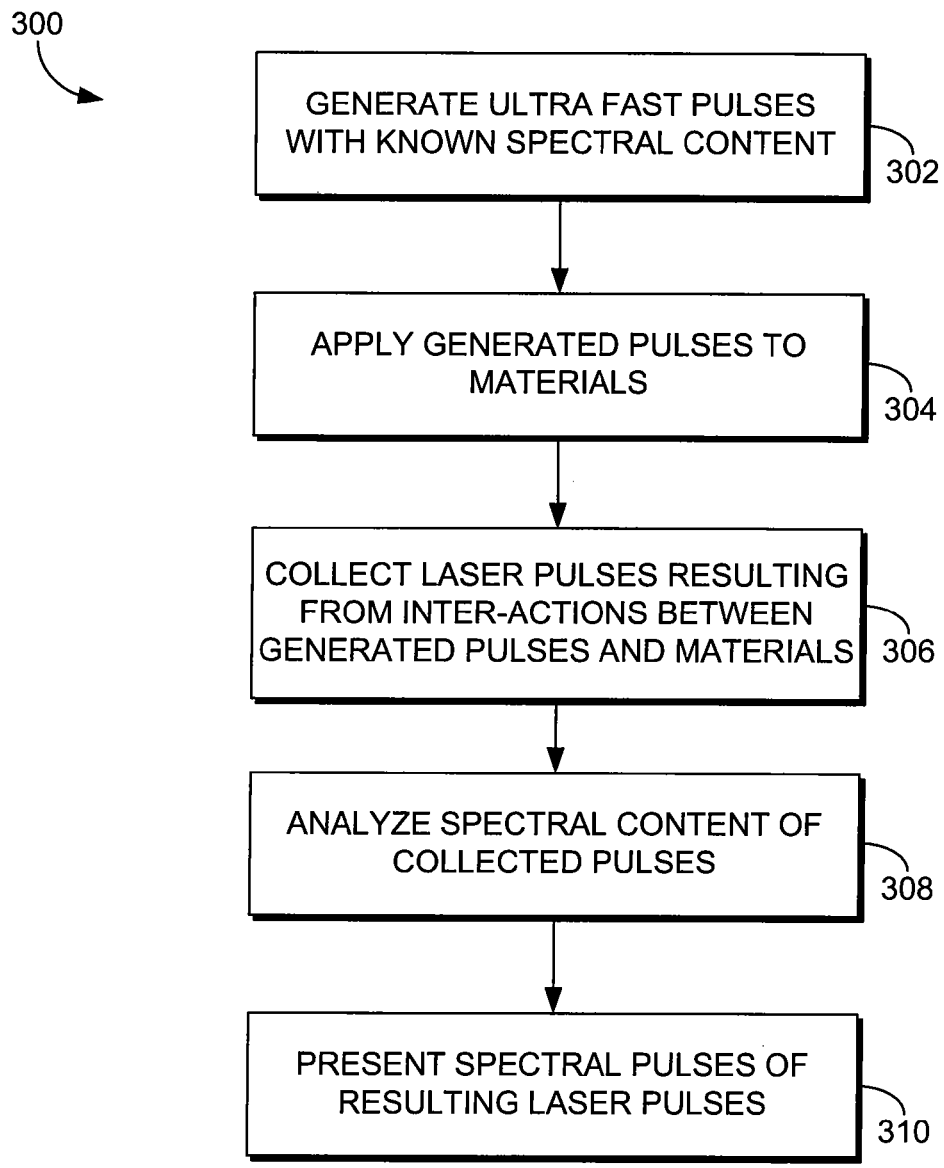
FIG. 3 is a flow diagram showing an exemplary method for monitoring a surface using ultra fast laser pulses in accordance with an embodiment of the present invention.

FIG. 3 shows a flow diagram illustrating an exemplary method for monitoring a surface using ultra fast pulses. In block 302, the ultra fast pulse generator generates ultra fast pulses. In some embodiments, the ultra fast pulses are one or several femtosecond laser pulses. In some embodiments, the ultra fast pulses are attosecond pulses. In block 304, the ultra fast pulses generated by the pulse generator are applied to the materials to be analyzed. In some embodiments, the materials to be analyzed may cover or coat the surface.

In block 306, the pulse detector collects resulting reflected pulses, scattered/transmitted pulses, or any combination thereof. In block, 308, the pulse detector generates spectral content of the resulting pulses. In some embodiments, the pulse detector may have an embedded module that generates the spectral content. In some embodiments, a spectral analyzer may be communicatively coupled to the pulse detector. In block 310, the spectral content of the resulting pulses is displayed. In some embodiments, the spectral content of the resulting pulses are compared to original spectral content of pulses produced by the pulse generator.

In one embodiment, for example, a 9 femtosecond (fs) laser pulse having a spectral spread of about 125 nano-meters (nm) around a central frequency of 800 nm is used to monitor an interfacial surface, providing 125 nm of wavelengths all at one time illuminating from the same laser pulse. This improves one of the shortcomings of the prior art that it is usually done at only one wavelength. The surface is illuminated with the 9 fs laser pulse first and the reflected laser pulse is collected. The physical dimensions of a 9 fs pulse is 2.7 micrometer (μm). For instance, one may illuminate a surface of interest with a short pulse, such as femtosecond or attosecond laser pulse, and observe the change in the spectral components as the electrons in the matter are excited to various excitation states. Depending on the materials that are present on the surface, the resulting spectral lines of the reflected laser pulse will change as the electrons in the materials are excited to various excitation states.

Figure 4:
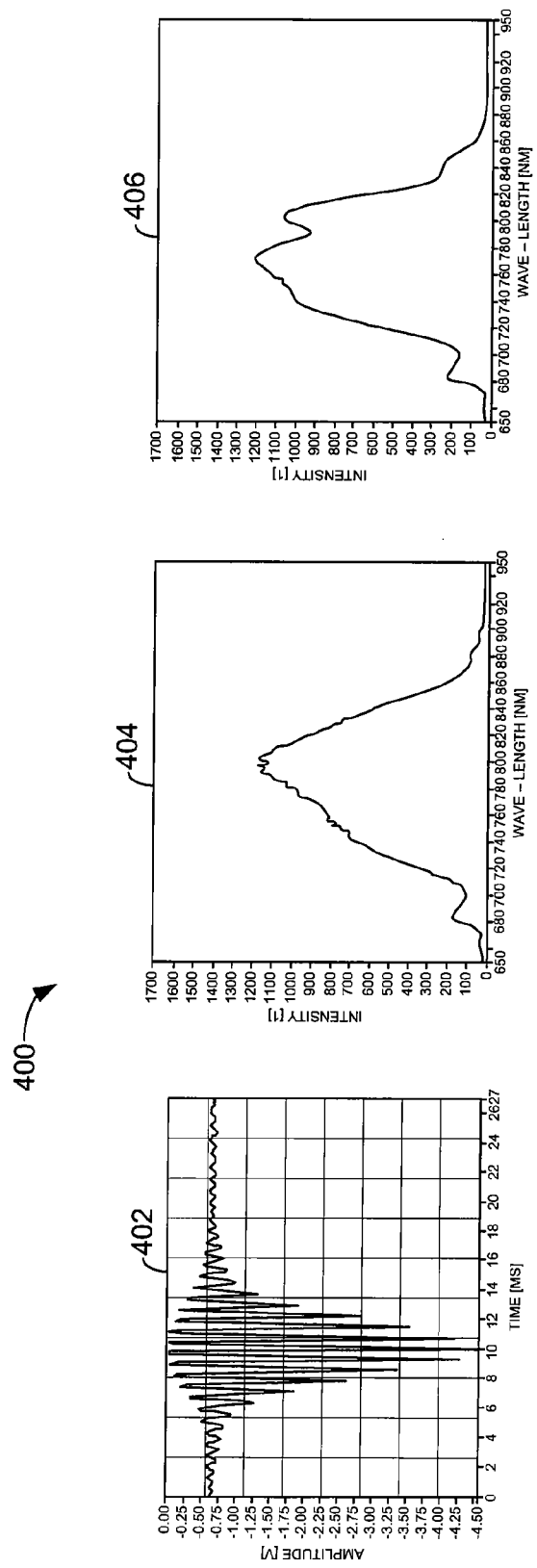
FIG. 4 shows a set of graphs illustrating images of autocorrelation trace of a femtosecond pulse and spectral content of the femtosecond pulses after reflected from different surfaces, respectively.

FIG. 4 shows a set of outcomes of non-contact metrology for evaluating the quality of silver mirrors using femtosecond laser pulses. FIG. 4 contains three images, left image 402, center image 404, and right image 406. The left image 402 is the autocorrelation trace of a typical 9-10 fs laser pulse. The center image 404 is spectral content of the pulse reflected from a high quality mirror. The right image 406 is spectral content of the pulse reflected from the same high quality mirror that has a thin dielectric coating on the surface of the mirror.

As can be seen from the center image 404 and the right image 406, some of the spectral lines of the reflected laser pulse in the right image 406 have changed from the spectral lines of the reflected laser pulse in the center image 404. The change in the spectral line content serves as a very sensitive method to monitor the surface of the mirror and the material components covering or making up the mirror surface. The same principle can be applied to silicon oxide ($SiO_2$)/SiC manufacturing stages.

For example, attosecond laser pulses, which are available in high energy laser facilities, gives ability to build a much more sensitive metrology instrument that would be sensitive to any silicon and carbon dangling bonds, carbon clusters and oxygen vacancies at a surface, such as a MOSFET surface that is being fabricated, resulting in improving the manufacturing of the SiC MOSFETs for high power operations. The size of the spot being integrated can be several millimeters to as small as the diffraction limit of the focusing devices used to probe a sample surface. In fact, if one does not occasionally mind sacrificing a control sample, it is possible to perform femtosecond laser induced breakdown spectroscopy (FLIBS) of the MOSFET surfaces being fabricated and determine the elemental composition of the interface nano layer by nano layer.

FLIBS analysis is destructive as the damage spot made by the ablation process is about 0.5 to 1 μm in size. The depth is controlled by the power used in the ablation but can be a small as a few nanometers. This method is only being proposed as a method for real time quality control where a few samples can be sacrificed during the manufacturing process. However, the information that can be obtained by this technique may prove valuable in improving the manufacturing of the SiC MOSFETs for high power operation.

Figure 5:
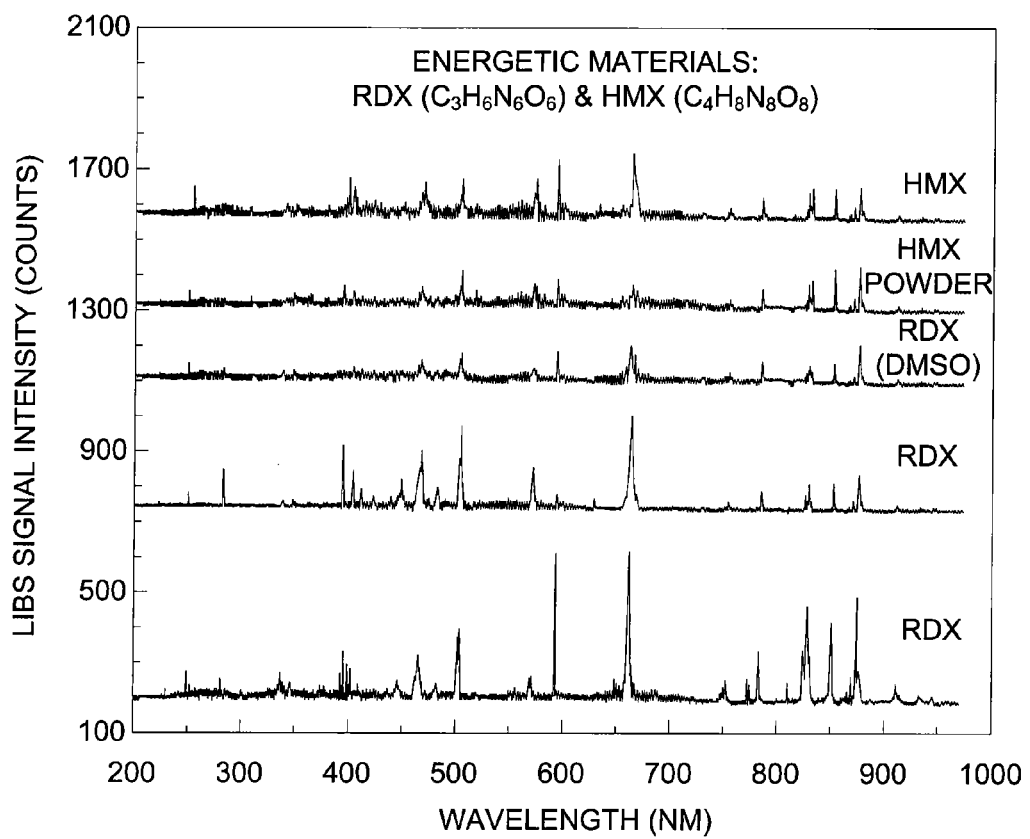
FIG. 5 illustrates typical LIBS signal from two different explosives containing only few difference compositions.
Figure 6:
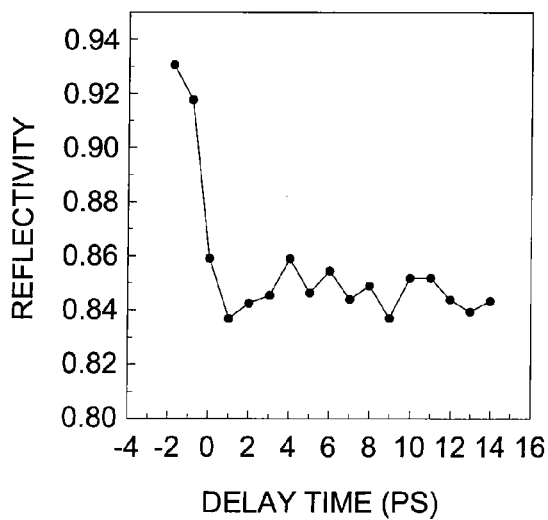
FIG. 6 illustrates time dependent reflectivity for an input pulse intensity of $1.5 \times 10^{12}$ W/cm$^2$.

It is important to point out that only in the last couple of years with the emergence of broad band spectrometers such as the Ocean Optics HR 4000+ and Andor system containing an Echelle spectrometer grating now makes it possible to determine chemical structures. FIG. 5 illustrates an example of the ability to distinguish some very similar but different chemical agents.

In some embodiments, pump-probing technique is performed using ultra fast femtosecond and attosecond laser pulses by varying the time delay between pump beam and probe beam in order to study the electron dynamics of the materials making up a surface or interfaces. For example, each interface layer of a MOSFET being fabricated can be analyzed. In one embodiment, the pump-probing technique is used to study the electron behavior in multilayered Co/Cu and Ag/Cu films. It can be demonstrated that the time dependent reflectivity of Cu films is due to the d-band transitions in Cu. This non-contact method is so sensitive that electronic transitions may be followed. FIG. 5 illustrates the time dependent reflectivity of Cu.

Problems with $SiO_2$/SiC interface result in part from the fact that carbon is a by-product of the oxidation process. The pump-probing technique combined with FLIBS analysis could provide more information about the exact nature of the oxidation processes, dangling bonds, and cluster information. Some interfacial defects have been speculated to include silicon and carbon dangling bonds, carbon clusters and oxygen vacancies at the interface. Interfacial passivation techniques involving annealing in NO and/or $H_2$ are currently used to lower the interface trap density ($D_{it}$) to levels around $10^{12}/cm^2$-cV. Despite recent progress, major challenges to SiC power MOSFETs include further decreasing $D_{it}$ increasing channel mobility while maintaining positive (normally-off) threshold voltages, improving the gate oxide reliability and achieving high threshold-voltage stability. It would be interesting to use the ultra fast pulses to passivate the surfaces as each one is deposited as a means to alter the $D_{it}$ concentration. Non-contact methods definitely have the capacity to answer some of the questions about the interfaces and the types of defects produced during the manufacturing processes and to provide some good feedback control required to have high quality SiC MOSFETs for high power applications.

Expansion of the proposed non contract metrology studies can be envisioned with the new high energy laser facilities, such as one being built at the University of Nebraska. This laser facility will mean that researchers at the University of Nebraska will have at there discretion a wide range of other types of non-contact ultra fast probe beams to apply to the SiC studies. Some interesting ultra fast probe sources beyond the laser pulse itself include strong femtosecond pulsed X rays, pulsed high energy electron beams, pulsed proton beams, and neutrons.

In order to perform capacitance-voltage characteristics non-contact measurements, the samples will be illuminated with laser beam below the damage thresholds. This illumination will create the necessary high fields approaching $10^6$ volts/cm. The exact location of illumination may be on the back side of the wafer and the fields measured over various parts of the device using scanning probe microscope tips. The current and voltages picked up by the SPM tips will be monitored as a function of time after the laser has applied the localized high fields. Another way is to induce the electrons by means of the pulses generated from the high energy laser facility. Another way is to use energy specific tailored protons that will loose all of their energy at the end of their paths in specific SiC structures. The voltages and currents will be monitored using a SPM tip. The leakage currents characteristics will be available as a function of time after the laser pulse induced the current.

One skilled in the art will appreciate that ultra fast pulse spectroscopy may be used to investigate any type of material, and will further appreciate that the type of pulse used may be varied as appropriate and desirable for a given material or application. For example, particular wavelengths of electromagnetic radiation, or particular types of pulsed particle beams, may be well suited to studying some materials or to study materials in some environments, while other types of pulses may be useful for other materials or in other environments. Such a varied use of ultra fast pulse spectroscopy does not depart from the scope of the present invention.

The invention claimed is:

1. A method for monitoring materials using ultra fast pulses, the method comprising:
applying ultra fast pulses having known spectral content to at least a portion of materials without applying pump pulses in addition to the ultra fast pulses to the portion of materials;
collecting pulses after interactions between the ultra fast pulses and the materials; and
analyzing the spectral content of the collected pulses to detect any change from the spectral content of the applied pulses, the spectral content comprising a distribution of intensity values across a range of wavelengths, and the analysis comprising detecting any change in the distribution of intensity values across the range of wavelengths in the collected pulses compared to those of the applied pulses.

2. The method of claim 1, further comprising generating the spectral content of the resulting pulses.

3. The method of claim 1, further comprising determining the elemental composition of the materials using the spectral content.

4. The method of claim 3, wherein determining the elemental composition of the materials using the spectral content comprises comparing the spectral content of the resulting pulses with original spectral content of the ultra last laser pulses.

5. The method of claim 1, wherein the ultra fast pulses comprise ultra fast laser pulses.

6. The method of claim 5, wherein the ultra fast laser pulses comprise femtosecond laser pulses.

7. The method of claim 5, wherein the ultra fast laser pulses comprise attoscecond laser pulses.

8. The method of claim 1, wherein the materials comprise interfacial surfaces.

9. The method of claim 1, wherein the materials comprise interfacial layers.

10. The method of claim 1, wherein the materials comprise nano layers.

11. The method of claim 1, wherein the materials comprise a combination of at least two of interfacial surfaces, interfacial layers, and nano layers.

12. The method of claim 1, wherein the materials are found on a MOSFET surface.

13. The method of claim 1, comprising analyzing changes in excitation states of the materials using differences between the spectral content of the collected pulses and the spectral content of the applied pulses.

14. The method of claim 1 in which applying ultra fast pulses to at least a portion of materials comprises applying ultra fast pulses to a cloud of materials.

15. The method of claim 14 in which applying ultra fast pulses to a cloud of materials comprises applying ultra fast pulses to a cloud of at least one of chemical compounds, biological compounds, chemical agents, or biological agents.

16. The method of claim 1, comprising analyzing an interface between a silicon oxide layer and a silicon carbide layer in a silicon carbide power metal-oxide semiconductor field effect transistor using differences between the spectral content of the collected pulses and the spectral content of the applied pulses.

17. The method of claim 1 in which applying ultra fast pulses comprises applying at least one of ultra fast pulsed X rays, pulsed high energy electron beam, pulsed proton beams, or pulsed neutron beams.

18. A system for monitoring materials using ultra fast laser pulses, the system comprising:
a pulse generator configured to generate ultra fast laser pulses and to apply the ultra fast laser pulses onto the materials without applying pump pulses in addition to the ultra fast laser pulses to the materials; and
a pulse detector configured to collect laser pulses resulting from interactions between the ultra fast laser pulses and the materials, and generate spectral content of the collected resulting laser pulses, the spectral content comprising a distribution of intensity values across a range of wavelengths;
wherein the pulse detector is further configured to analyze the spectral content of the collected pulses to detect any change in the distribution of intensity values across the range of wavelengths in the collected pulses compared to those of the applied pulses.

19. The system of claim 18, wherein the pulse detector is further configured to present the spectral content.

20. The system of claim 18, wherein the pulse detector is further configured to determine the elemental composition of the materials using the spectral content.

21. A method for monitoring materials using ultra fast laser pulses comprising:
performing pump-probing techniques on the materials by varying the time delay between a pump beam and a probe beam, wherein the pump beam and the probe beam comprise ultra fast lasers;
detecting the probe beam reflected from the materials to determine time dependent reflectivity of the materials;
identifying a change in reflectivity that corresponds to one or more electron transitions in the materials as the amount of time delay is increased, and
analyzing electron transitions in the materials using the chance in reflectivity of the materials for various time delays.

22. The method of claim 21, wherein the pump beam comprises a femtosecond laser.

23. The method of claim 21, wherein the pump beam comprises an attosecond laser.

24. The method of claim 21, wherein the probe beam comprises a femtosecond laser.

25. The method of claim 21, wherein the probe beam comprises an attosecond laser.

26. The method of claim 21 in which analyzing electron transitions in the materials comprises analyzing electron transitions in at least one of multilayered Co/Cu or multilayered Ag/Cu films.

27. The method of claim 21 in which identifying a change in reflectivity comprises identifying a modification in reflectivity for the range of spectral content being detected.

* * * * *

UNITED STATES PATENT AND TRADEMARK OFFICE
CERTIFICATE OF CORRECTION

PATENT NO. : 8,189,190 B2
APPLICATION NO. : 11/848886
DATED : May 29, 2012
INVENTOR(S) : Dennis R. Alexander It is certified that error appears in the above-identified patent and that said Letters Patent is hereby corrected as shown below:

Col. 6, claim 4, line 49, delete "last" and insert -- fast --.

Col. 6, claim 7, line 56, delete "attosceond" and insert -- attosecond --.

Signed and Sealed this
Seventh Day of August, 2012

David J. Kappos
*Director of the United States Patent and Trademark Office*